US005091179A

United States Patent [19]

Biache et al.

[11] Patent Number: 5,091,179
[45] Date of Patent: Feb. 25, 1992

[54] INSECTICIDE BASED ON A VIRUS FROM THE BACULOVIRUS GROUP, AND USE THEREOF FOR THE DESTRUCTION OF PHTHORIMAEA OPERCULELLA

[75] Inventors: Gerard A. Biache, Guyancourt; Michel R. Guillon, Beziers, both of France

[73] Assignee: Calliope S.A., Beziers, France

[21] Appl. No.: 281,737

[22] Filed: Dec. 9, 1988

[30] Foreign Application Priority Data

Dec. 18, 1987 [FR] France ................................ 87 17748

[51] Int. Cl.$^5$ .............................................. A01N 63/00

[52] U.S. Cl. ................................ 424/93 T; 435/235.1

[58] Field of Search ............... 424/93; 435/235, 240.1, 435/235.1

[56] References Cited

U.S. PATENT DOCUMENTS

| | | | |
|---|---|---|---|
| 3,639,578 | 2/1972 | Batzer | 424/93 |
| 3,702,359 | 11/1972 | Dulmage et al. | 424/93 |

OTHER PUBLICATIONS

H. D. Burges et al.; Microbial Control of Insects and Mites, 1971, pp. 497–499; 555; 623–629; 647–654; 688–689.

CAB, No. 87081830; R. Balgurunthan et al.; Mass Rearing of Mamestra Brassicae.

*Primary Examiner*—Richard A. Schwartz
*Assistant Examiner*—S. L. Nolan
*Attorney, Agent, or Firm*—Finnegan, Henderson, Farabow, Garrett & Dunner

[57] ABSTRACT

The invention is a method for destroying *Phthorimaea operculella* by causing the *Phthorimaea operculella* to ingest the baculovirus of the nuclear polyhedrose of the noctuid *Mamestra brassicae.*

10 Claims, No Drawings

INSECTICIDE BASED ON A VIRUS FROM THE BACULOVIRUS GROUP, AND USE THEREOF FOR THE DESTRUCTION OF PHTHORIMAEA OPERCULELLA

The present invention relates to an insecticide agent active against *Phthorimaea operculella*, an insecticide composition containing this agent, a method of preparing the latter and a method of destroying *Phthorimaea operculella*.

*Phthorimaea operculella* is a parasite of cultivated solanaceous plants such as potatoes, tobacco, tomatoes and aubergines. Thus, it is commonly called potato mite or tobacco leaf miner. The caterpillars of this parasite feed on the plants on which they develop and man has always fought against these harmful insects. For this, use has in particular been made of chemical insecticides whose toxicity with regards to vertebrae in general and Man in particular leads however to having to take strict precautions in use.

Thus, the aim of the present invention is to provide an insecticide inoffensive for vertebrae and plants and which may be termed biological. This invention is based on the surprising discovery that the natural virus (baculovirus of nuclear polyhedrose) of the noctuid *Mamestra brassicae* (cabbage parasite) when it is ingested by the *Phthorimaea operculella* caterpillars causes considerable mortality among these caterpillars.

Consequently, the first object of the present invention resides in an insecticide agent active against *Phthorimaea operculella*, which is characterized in that it is formed by the baculovius of the nuclear polyhedrose of the noctuid *Mamestra brassicae*.

Since the baculoviruses generally have a very specific viral activity, it is quite unexpected that the particular baculovirus used in the present invention has an activity with respect to a parasite, the *Phthorimaea operculella* caterpillar, so different from the caterpillar of the noctuid *Mamestra brassicae*. In fact, *Phthorimaea operculella* and *Mamestra brassicae* belong to different families, the first belonging to the family of the noctuidae and the second to the family of the Gelechiidae. Moreover, the baculovirus of *Mamestra brassicae* and the natural virus of *Phthorimaea operculella* have different taxonomic positions since the first enters in to the sub-group of the viruses of nuclear polyhedroses whereas the second enters into the sub-group of the viruses of granulosis. It is also important to note that, since the geographical areas in which *Mamestra brassicae* and *Phthorimaea operculella* are present are very different, there cannot be natural mortality of *Phthorimaea operculella* due to the presence of the *Mamestra brassicae* virus. A second object of the present invention resides in an insecticide composition active against *Phthorimaea operculella*, this composition being characterized in that it comprises, as active substance, the above defined insecticide in an appropriate vehicle.

This insecticide composition may be in different forms. Thus, it may for example be in the form of a suspension of said insecticide agent in a liquid vehicle containing possibly a dispersant, this liquid vehicle being chosen preferably from the group comprising water, vegetable oils (particularly cotton oil) and mixtures thereof. It may in a variant be in the form of a powder comprising said insecticide agent and a powdery vehicle such as talc. Of course, this composition may if desired also contain other additives, e.g. additives capable of improving adherence.

The present invention further has as object a method of preparing the above defined insecticide agent, this method being characterized in that it comprises the steps which consist:

(a) in contaminating *Mamestra brassicae* caterpillars in the last but one larval stage with the baculovirus of the nuclear polyhedrose of the noctuid *Mamestra brassicae*, and (b) extracting from the caterpillars which have died following such contamination the baculoviruses which have increased therein.

Advantageously, step (a) of this method consists in causing said caterpillars to ingest a nutritional medium contaminated with said baculoviruse, this medium comprising preferably the following nutritional elements: cabbage powder, beer yeast, crushed maize, crushed wheat germ, casein hydrolysate, mineral salts.

As for step (b) of this method, it preferably comprises the crushing of the dead caterpillars and the filtration of the slurry resulting from such crushing, on a filter having a mesh opening capable of retaining particles of a dimension greater than 0.3 μ and particularly the polyhedres of the baculovirus which have a dimension of 0.5 to 2.5 μ, such filtration being followed by elimination of the liquid phase of the filtrate. Such elimination may in particular be carried out by acetonic precipitation int he presence of lactose, lyophilisation or spray drying.

The present invention finally has as object a method of destroying *Phthorimaea operculella* infesting the foliage, the tubercles, the fruits and/or the flower buds of cultivated solanaceous plants, this method being characterized in that it consists in applying the above defined insecticide agent or insecticide composition on said foliage, tubercles, fruits and/or flower buds. When the insecticide composition is used in the form of a suspension, it is preferably applied on the foliage, fruits and/or flower buds at the rate of $1.10^{13}$ to $5.10^{13}$ polyhedres/hectare of foliage, fruits and/or flower buds and when it is used in the form of a powder, the latter is preferably deposited by powdering on the tubercles at the rate of $1.10^{9}$ to $10.10^{9}$ polyhedres/g of tubercles.

The following non limitative examples are given by way of illustration of the present invention.

EXAMPLE 1

Production of the baculovirus of the nuclear polyhedrose of the noctuid *Mamestra brassicae.*

*Mamestra brassicae* caterpillars are raised on an artificial nutritional medium (M) described in example 2, until the last but on larval stage. They are then infected by ingesting an artificial nutritional medium (M') described in example 3, contaminated by the baculovirus of the nuclear polyhedrose of the noctuid *Mamestra brassicae*. The contaminated caterpillars die within 9 to 10 days. The bodies are then crushed and filtered for example on a glass fiber filter having a mesh size capable of retaining all particles of a dimension greater than 0.3 μ. On the filtrate, an acetonic precipitation is carried out by adding thereto four volumes of acetone for one volume of filtrate and lactose at the rate of 6% by weight of the filtrate and by subjecting the resultant mixture to energetic agitation for homogenizing it. As a variant, the filtrate may be lyophilized or subjected to spray drying. The powder thus obtained contains the desired baculoviruses plus cellular waste. The activity of the preparations obtained as described above is determined by a series of counts using a hematimetric cell which makes it possible to count an average number of polyhedres, then by biological tests measuring the insecticide activity on caterpillars.

EXAMPLE 2

Composition of the nutritional medium (M) mentioned in example 1.

For 1 kg of this nutritional medium, the following are used:

| Binders (A) | |
| --- | --- |
| agar—agar | 16 g |
| distilled water | 780 ml |
| Nutritional elements (B) | |
| cabbage powder | 64 g |
| beer yeast | 34 g |
| crushed maize | 64 g |
| crushed wheat germ | 32 g |
| casein hydrolysate | 5 g |
| saline mixture | 3.5 g |
| Antimicrobial agents (B') | |
| benzoic acid | 2.5 g |
| Nipagine (C) = Methyl parahydroxybenzoate | 1.1 g |
| Formaldehyde (D) | 0.5 ml |
| Vitamins (E) | |
| vitamin mixture | 3 g |
| ascorbic acid | 4.5 g | the agar-agar is dissolved in half the amount of water indicated, at 120° C. for 20 minutes in autoclave.

Meanwhile, the powders B and B' are mixed with the remaining water; the methyl parahydroxybenzoate (C) is dissolved in 5 ml of 90° alcohol.

When the gelose is dissolved it is incorporated in the nutritional elements (B) and (B') using a household type mixer. The temperature of the mixture then drops rapidly to 55° C., at which temperature the antimicrobial agents (C) and (D) and the vitamins (E) can be included.

The mixture, still hot, is distributed in the different raising devices and rapidly hardens when cooling.

It may be kept in closed boxes for 8 to 10 days at 5° C.

EXAMPLE 3

Composition of the nutritional medium (M') mentioned in example 1.

This medium is also used for the biological tritration tests. For a kilogram of medium the following are used: agar-agar 12 g, water 800 ml, cabbage powder 64 g, beer yeast 34 g, maize 64 g, wheat germ 32 g, benzoic acid 2.5 g, nipagine 1.1 g, ascorbic acid 4.5 g.

EXAMPLE 4

Treatment against potato mite.

The strain of the ravager used for the experiments comes from the Dar Bouazza region of Casablanca (Morocco). This strain is raised on potato tubercles, at a temperature of 25° C.

A test was carried out on potato leaves. *Phthorimaea operculella* moths from Morocco are placed for laying in a cage containing branches with leaves and after 48 hours the eggs are counted. Then, on the leaves is sprayed, in a treatment tower a suspension in water of the virus prepared in accordance with example 1 and at two different doses of the virus, namely at the dose of 50 polyhedres/mm$^2$ of foliage (dose 1) and at the dose of 250 polyhedres/mm$^2$ of foliage (dose 2). The lethal activity of this suspension is evaluated by counting the number of moths formed from the eggs. The results obtained are the following:

| untreated control | 65 eggs lead to 54 moths: about 17% mortality |
| --- | --- |
| baculovirus dose 1 | 51 eggs lead to 37 moths: about 28% mortality |
| baculovirus dose 2 | 51 eggs lead to 17 moths: about 60% mortality |

With this method of treatment, action of the virus related to the dose can be observed.

Furthermore, several tests wee carried out on potato tubercles using respectively a powder formed of 98% by weight of talc and 2% of the baculovirus prepared in accordance with example 1 and having a viral activity of $72.10^9$ polyhedres/g and a powder formed of 90% by weight of talc and 10% by weight of the same baculovirus. The amount of powder used represented 1% of the weight of the tubercles. The tubercles were treated by coating them with the above powders and the lethal activity of these powders was determined by counting the number of moths formed from the eggs laid in 24 hours by 30 *Phthorimaea operculella* moths. The results obtained are as follows:

| untreated control | 100% of the eggs laid led to the formation of a moth |
| --- | --- |
| powder dosed at 2% | 26% only of the eggs laid led to the formation of a moth (mortality rate 74%) |
| powder dosed at 10% | 9% only of the eggs laid led to the formation of a moth (mortality rate 91%). |

The above tests were repeated four times using an untreated control and the powder dosed at 2% and the following percentages of moths were observed: control: 100%; powder dosed at 2%: 5%, 12%, 8% and 23%.

The above results undeniably demonstrate the powerful insecticide activity of the compositions tested.

We claim:

1. A method for destroying *Phthorimaea operculella* comprising the step of causing the *Phthorimaea operculella* to ingest the baculovirus of the nuclear polyhedrose of the noctuid *Mamestra brassicae*.

2. The method of claim 1, wherein the baculovirus of the nuclear polyhedrose of the noctuid *Mamestra brassicae* is used in the form of a suspension in an appropriate liquid vehicle.

3. The method of claim 1, wherein the baculovirus of the nuclear polyhedrose of the noctuid *Mamestra brassicae* is used in the form of a mixture with a powdery vehicle.

4. A method for the destruction of *Phthorimaea operculella* infesting the foliage, the tubercles, the fruits or the flower buds of cultivated solanaceous plants, which comprises applying the baculovirus of the nuclear polyhedrose of the noctuid *Mamestra brassicae* on said foliage, tubercles, fruits or flower buds.

5. The method of claim 4, wherein the baculovirus of the nuclear polyhedrose of the noctuid *Mamestra brassicae* is used in the form of a suspension in an appropriate liquid vehicle and is applied to the foliage, fruits or flower buds of said plants.

6. The method of claim 5, wherein said liquid vehicle is selected from the group consisting of water, vegetable oils and mixtures thereof.

7. The method of claim 5 or 6, wherein said suspension is applied at the rate of $1.10^{13}$ to $5.10^3$ polyhedres/hectare of said foliage, fruits or flower buds.

8. The method of claim 4, wherein the baculovirus of the nuclear polyhedrose of the noctuid *Mamestra brassicae* is used in the form of a mixture with a powdery vehicle and is applied to the tubercles of said plants.

9. The method of claim 8, which comprises powdering the tubercles with said mixture at the rate of $1.10^9$ to $10.10^9$ polyhedres/g of tubercles.

10. An insecticide composition for destroying *Phthorimaea operculella* comprising as the active ingredient the baculovirus of the nuclear polyhedrose of the noctuid *Mamestra brassicae*.

* * * * *